US012262986B2

(12) United States Patent
Kimple et al.

(10) Patent No.: US 12,262,986 B2
(45) Date of Patent: Apr. 1, 2025

(54) LESION VOLUME MEASUREMENTS SYSTEM

(71) Applicant: Wisconsin Alumni Research Foundation, Madison, WI (US)

(72) Inventors: Randall Joel Kimple, Madison, WI (US); Junzhou Chen, Madison, WI (US); Hunter Alexander Higby, Belleville, WI (US); Ryan Wisth, Madison, WI (US); Kyuhyun Lee, Gyeonggi-do (KR); Jeremy David Rogers, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 591 days.

(21) Appl. No.: 16/998,797

(22) Filed: Aug. 20, 2020

(65) Prior Publication Data
US 2021/0052189 A1    Feb. 25, 2021

Related U.S. Application Data

(60) Provisional application No. 62/890,384, filed on Aug. 22, 2019.

(51) Int. Cl.
*A61B 5/06* (2006.01)
*A61B 5/00* (2006.01)
*A61B 90/00* (2016.01)

(52) U.S. Cl.
CPC .............. *A61B 5/06* (2013.01); *A61B 5/0079* (2013.01); *A61B 5/742* (2013.01); *A61B 90/06* (2016.02);
(Continued)

(58) Field of Classification Search
CPC ............ A61B 5/0079; A61B 2090/063; A61B 2090/3618; A61B 5/1073; A61B 5/742; A61B 2090/363; A61B 5/06; A61B 90/36; A61B 5/0073; A61B 5/1079; A61B 90/06; A61B 6/02; A61B 2503/40
(Continued)

(56) References Cited

U.S. PATENT DOCUMENTS 5,146,923 A * 9/1992 Dhawan ................. A61B 5/444
                                                         600/476
8,068,650 B2 * 11/2011 Kumar .................. A61B 6/5247
                                                         600/407
(Continued)

FOREIGN PATENT DOCUMENTS

DE       112020002467 T5 *  3/2022   ............. A61B 34/20
WO    WO-2018029286 A1 *  2/2018   ........... A61B 5/0053
WO         2018229360 A1    12/2018

OTHER PUBLICATIONS

S. A. Nene and S. K. Nayar, "Stereo with mirrors," Sixth International Conference on Computer Vision (IEEE Cat. No. 98CH36271), 1998, pp. 1087-1094, doi: 10.1109/ICCV.1998.710852. (Year: 1998).*

*Primary Examiner* — Patrick Fernandes
*Assistant Examiner* — Jonathan E. Cooper
(74) *Attorney, Agent, or Firm* — Boyle Fredrickson, SC

(57) ABSTRACT

An apparatus for measuring lesion volume, for example, in laboratory animals, provides a mirror box allowing a camera to simultaneously acquire profiles of the lesion along at least two crossing axes from which accurate volume may be approximated at low cost.

20 Claims, 4 Drawing Sheets

(52) U.S. Cl.
CPC ........ *A61B 90/36* (2016.02); *A61B 2090/063* (2016.02); *A61B 2090/363* (2016.02); *A61B 2503/40* (2013.01)

(58) Field of Classification Search
USPC ....................................................... 600/587
See application file for complete search history.

(56) References Cited

U.S. PATENT DOCUMENTS

| | | | |
|---|---|---|---|
| 10,318,976 B2 | 6/2019 | Hendrick | |
| 2003/0026110 A1* | 2/2003 | Satoh | A61B 5/442 348/E5.029 |
| 2004/0034301 A1* | 2/2004 | Falco | A61N 5/1049 600/427 |
| 2009/0161827 A1* | 6/2009 | Gertner | A61N 5/1017 378/65 |
| 2010/0042004 A1* | 2/2010 | Dhawan | A61B 5/444 600/476 |
| 2010/0128952 A1* | 5/2010 | Schmitt | G06T 5/008 382/131 |
| 2012/0172685 A1* | 7/2012 | Gilbert | A61B 5/0077 600/306 |
| 2013/0030250 A1* | 1/2013 | Findeisen | A61B 1/00096 600/165 |
| 2015/0196369 A1* | 7/2015 | Glossop | A61B 8/12 600/417 |
| 2016/0166194 A1* | 6/2016 | Gareau | A61B 5/14552 600/328 |
| 2016/0310582 A1* | 10/2016 | Sandler | A61K 39/0011 |
| 2017/0251932 A1* | 9/2017 | Kaku | A61B 5/02007 |
| 2017/0265828 A1* | 9/2017 | Tsujii | A61B 5/0091 |
| 2017/0340023 A1 | 11/2017 | McKeen et al. | |
| 2018/0092694 A1* | 4/2018 | Zhang | A61B 18/201 |
| 2018/0144467 A1* | 5/2018 | Sofka | A61B 5/4064 |
| 2019/0209074 A1* | 7/2019 | Westerhof | A61B 5/0079 |
| 2020/0327670 A1* | 10/2020 | Connor | G06T 7/62 |

\* cited by examiner

LESION VOLUME MEASUREMENTS SYSTEM

CROSS REFERENCE TO RELATED APPLICATION

This application claims the benefit of U.S. provisional application 62/890,384 filed Aug. 22, 2019 and hereby incorporated in its entirety by reference.

STATEMENT REGARDING FEDERALLY SPONSORED RESEARCH OR DEVELOPMENT

This invention was made with government support under DE026787 awarded by the National Institutes of Health. The government has certain rights in the invention.

BACKGROUND OF THE INVENTION

The present invention relates to instruments for measuring the volume of lesions, for example, tumors in laboratory animals, and in particular to a low-cost optical system for lesion volume measurement.

Tracking the volume of tumors produced by subcutaneously implanted cancers in mice is used to determine the efficacy of anticancer treatments. Early signs of successful treatment are indicated by tumor shrinkage.

Unfortunately, the standard approach to measuring tumor volume uses mechanical calipers which are subject to substantial intra-user variation, often as high as 10 to 20 percent. This low accuracy can obscure the effects of the anticancer drug if not compensated by increasing the number of animals tested with a concomitant increase in time and costs.

More precise methods of lesion volume measurement can be performed using advanced medical imaging technologies such as ultrasound or CT scanning or by mapping the surface of the tumor using structured light and stereo cameras imaging techniques. These techniques are relatively expensive, however, and for this reason caliper measurements are still widely used.

SUMMARY OF THE INVENTION

The present invention provides a low-cost volume measurement system for lesions using a single camera in conjunction with a "mirror cone," the latter allowing the camera to obtain multiple side views of the lesion when the camera is directed downward on the lesion. A top view by the camera allows consistent alignment, and the side views are processed to provide an estimate lesion volume with a precision superior to current caliper techniques.

More specifically, in one embodiment, the invention provides an apparatus for measuring the volume of lesions, the invention including a housing providing a lower surface adapted to be positioned and supported at a surface of the skin around the lesion with the lesion extending upwardly through a center opening in the lower surface. An electronic camera is directed toward the center opening along a camera axis as held by the housing at a predetermined distance from the lower surface. A first mirror is attached to the housing and angled to provide a side view of a lesion extending upward through the center opening along a first mirror axis in a plane substantially parallel to the surface of the skin, and a second mirror is attached to the housing and angled to provide a side view of a lesion extending upward through the center opening along the second mirror axis in the plane and different from the first mirror axis. An electronic computer executes a program stored in non-transitory memory to receive an image from the camera of side views from the first and second mirrors to compute a volume of the lesion.

It is thus a feature of at least one embodiment of the invention provide a simple and low-cost way of measuring tumor volume subject to less operator variability.

The first and second mirrors furthest from the electronic camera may provide reflecting surface within one-quarter inch of the surface of the skin.

It is thus a feature of at least one embodiment of the invention to provide side profiles capturing the base of the tumors that would be difficult to obtain directly using a camera.

The volume computation may compute the volume of the lesion from the sum of a set of slices parallel to the plane at different heights along the lesion and displaced along the camera axis, each slice constrained in width across the first mirror axis and second mirror axis by a width of the side view from the respective mirror at the height.

It is thus a feature of at least one embodiment of the invention to increase the number of measurements beyond the two measurements normally performed with calipers to provide improved accuracy in the measurement of tumors that cannot be closely approximated by simple solids like an ellipsoid.

The constraining width of the slices may be fit to a closed curve to define the slice perimeter, wherein the closed curve is an ellipse, the first and second mirror axes are perpendicular and define the major and minor axes of the ellipse, respectively.

It is thus a feature of at least one embodiment of the invention to provide improved measure of volume based on a tendency for lesions to have a rounded shape.

The apparatus may include a display displaying an image from the electronic camera having at least one fiducial superimposed on the image of a top view of a lesion extending upwardly through the central opening, the fiducial mark adapted to allow alignment of the tumor with the at least one fiducial mark between successive measurements of the tumor by the apparatus.

It is thus a feature of at least one embodiment of the invention to permit accurate registration of the lesion centered within the opening for improved repeatability of volume measurements in longitudinal studies.

The apparatus may provide at least two fiducial marks to allow both a centering of the lesion within the plane and a predetermined rotational orientation of the lesion about the camera axis.

It is thus a feature of at least one embodiment of the invention to reduce variability that can come from rotation of the lesion profile views with respect to the lesion.

The housing may provide an opaque shroud around the central opening and further include a diffuse illuminator positioned to illuminate a lesion extending upwardly through the central opening, the diffuse illuminator being a ring light.

It is thus a feature of at least one embodiment of the invention to provide improved imaging of the profiles of the lesion possible in a controlled illuminated environment free from variability imposed by outside light sources.

The apparatus in some embodiments may include at least a third mirror attached to the housing and angled to provide a side view of a lesion along the third mirror axis in the plane and different from the first and second mirror axes; and the electronic computer may receive an image from the camera of side views from the first and second and third mirrors to compute a volume of the lesion.

It is thus a feature of at least one embodiment of the invention to provide improved accuracy through multi-angle imaging without the need for complex systems for moving a camera or sensor about the lesion.

The apparatus may include a display communicating with the electronic computer to display at least one image of the lesion together with a computed volume.

It is thus a feature of at least one embodiment of the invention to provide an immediate readout of volume linked to an image for later confirmation and validation.

The apparatus may store a set of images taken at different times together with volumes of the lesions derived from those images.

It is thus a feature of at least one embodiment of the invention to permit review of qualitative changes of the lesion visible in the image and not only quantitative changes in the volume.

The apparatus may provide video display sequencing through the set of images.

It is thus a feature of at least one embodiment of the invention to provide a set of consistently obtained images of the lesion that may reveal other changes in the lesion shape or morphology.

These particular objects and advantages may apply to only some embodiments falling within the claims and thus do not define the scope of the invention.

DETAILED DESCRIPTION OF THE PREFERRED EMBODIMENT

Figure 1:
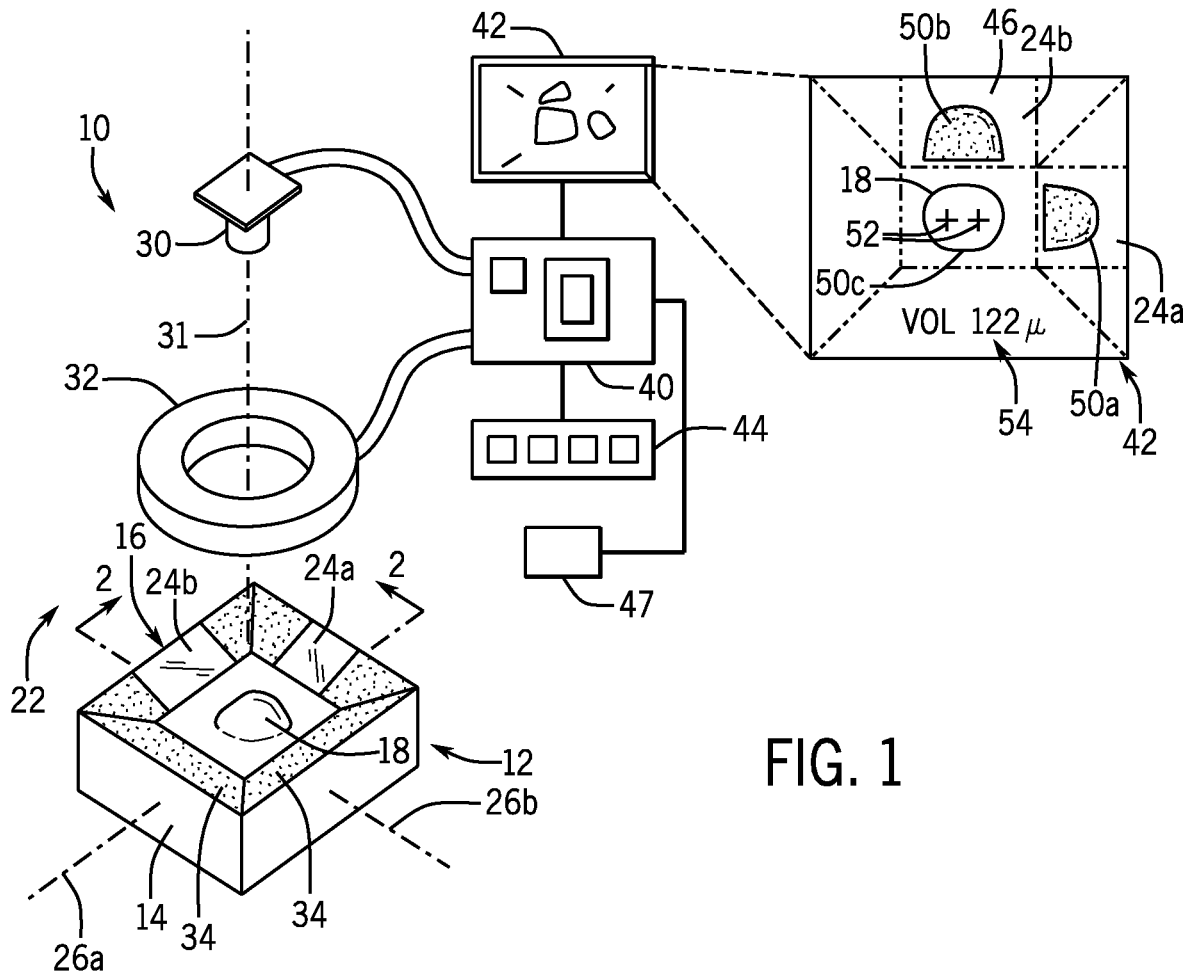
FIG. 1 is an exploded perspective view of a camera and mirror cone of the present invention as may communicate with a processor and display the latter displaying a top view and two side views of a lesion as shown in an inset.

Referring now to FIG. 1, an instrument 10 for lesion volume measurement according to one embodiment of the present invention may provide for a mirror cone 12 having a housing 14 providing a central opening 16. The central opening 16 is sized to permit a lesion 18 on the skin to extend upwardly through the central opening when the housing 14 is pressed down onto the skin around the lesion 18.

Figure 2:
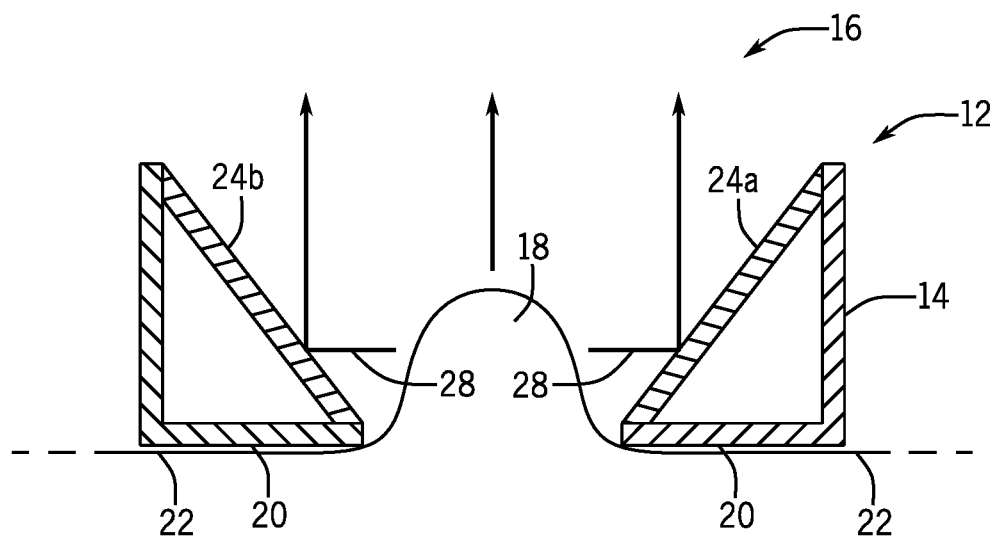
FIG. 2 a cross-sectional view taken along line 2-2 of FIG. 1 of the mirror cone positioned about a lesion showing ray paths through the mirrors of the mirror cone to the camera.

Referring also to FIG. 2, in this regard, the housing 14 may provide for a lower foot surface 20 that may be positioned to abut or closely abut skin at the skin plane 22 around the lesion 18 such as may help isolate the lesion 18 and raise it upward through the central opening 16. In one embodiment, the lower foot surface 20 may provide for a broad contact area along the skin plane 22, for example, exceeding two square inches surrounding the central opening 16 so as to stabilize the instrument 10 with respect to a well-defined skin plane 22 and to flatten the skin plane around the lesion 18.

The upper surface of the mirror cone 12 in one embodiment may be upwardly concave presenting a surface conforming to a downward frustum of a rectangular pyramid centered over the central opening 16. The surface may support at least two mirrors 24a and 24b positioned to the side of the lesion 18 when the lesion is positioned within the central opening 16. Each of the mirrors 24a and 24b are displaced from a center of the lesion along perpendicular axes 26a and 26b generally parallel to the skin plane 22. The mirrors 24a and 24b are angled at approximately 45° from the skin plane 22 so as to direct light received along ray lines 28 from the lesion and generally parallel to the skin plane 22 upward toward a camera 30.

Referring still to FIGS. 1 and 2, the camera 30 may be supported above the central opening 16 and have a field of view directed downward toward the opening 16 so that a central axis 31 of its field-of-view is centered within the opening 16 and can capture not only the lesion 18 but the mirrors 24 on either side of the lesion 18. The camera 30 may, for example, provide for 1080 P progressive scanning with 3280×2464 pixels and an angle of view of approximately 62×48 degrees. Depending on the field of view of the camera 30, the mirrors 24 may have an angle slightly more than 450 with respect to the skin plane 22 so as to preserve the parallel nature of ray lines 28.

Generally, the camera 30 will be able to image the lesion 18 in the top plan view directly and in two perpendicular side views through reflections of the mirrors 24. The camera 30 may be fixed with respect to the housing 14 to be properly focused on the lesion 18 by the spacing between the camera and the lower foot surface 20.

In one embodiment, the mirrors 24 may be front surface mirrors and/or may have a lowermost mirror reflecting edge within ¼ of an inch and preferably within ⅛ or less than ¹⁄₁₆ of an inch from the skin plane 22 so as to capture the complete lesion 18 above the skin plane. In this regard, the upper edge of the mirrors may extend by at least ½ inch and preferably at least ¾ of an inch or at least 1 inch above the skin plane 22 to capture the full height of a range of sizes of lesion 18. The central opening 16 may be sized for the particular lesion but will generally be at least one square inch in area and as much as 12 square inches in area. The central opening may in some embodiments be circular or ovoid to provide close conformance to typical lesions 18.

Portions of the upper surface of the mirror cone 12 facing the camera 30 outside of the mirrors 24 may be coated with a dark (e.g., black) nonreflective material 34 or may be constructed of a dark nonreflective material, for example, using an appropriately colored thermoplastic to provide good contrast in the imaging process. In the embodiment shown, each mirror 24 may provide an image of the lesion 18 against a dark background formed by an opposite side of the mirror cone 12.

Referring still to FIG. 1, the invention may provide a diffuse light source 32, for example, a light ring of white light or near infrared light or ultraviolet light emitting diodes arranged in a circle about the axis (camera axis) and positioned behind a diffuser of translucent plastic or the like. The diffuse light source 32 may be positioned above the mirror cone 12 to provide downward diffuse illumination of the positioned lesion 18 with the camera 30 oriented to image through a center of the diffuse light source 32.

The camera 30 and the diffuse light source 32 may communicate with a microcontroller board 40, for example, a Raspberry Pi 3 Model B Motherboard commercially available from the Raspberry Pi Foundation of the United Kingdom. Generally, the microcontroller board 40 may include one or more processors and electronic memory holding a stored program whose operation will be described below. During operation of the instrument 10, the microcontroller board 40 may turn the camera 30 and diffuse light source 32 on and off and may receive video signals from the camera 30. The microcontroller board 40 may also communicate with a screen 42, for example, for providing graphic and text output and being constructed, for example, of a standard LCD display module or the like. In some embodiments, the screen 42 may be a touchscreen or the microcontroller board 40 may communicate with a set of switches 44 for controlling the instrument 10. The instrument 10 may further include a battery 47 for powering recited components and operating portably.

In a first mode, the screen 42 may provide a concurrent display of an image 46 from the camera 30 showing a first profile 50a and second profile 50b of the lesion 18 and a top plan view 50c. Superimposed on the top plan view may be a first and second alignment mark 52 that may be aligned with fiducial marks, for example, tattoos or ink marks placed on the lesion 18 to ensure consistent alignment of the camera and the lesion 18. The image 46 may also provide for volume display 54 as will be discussed in greater detail below.

Figure 3:
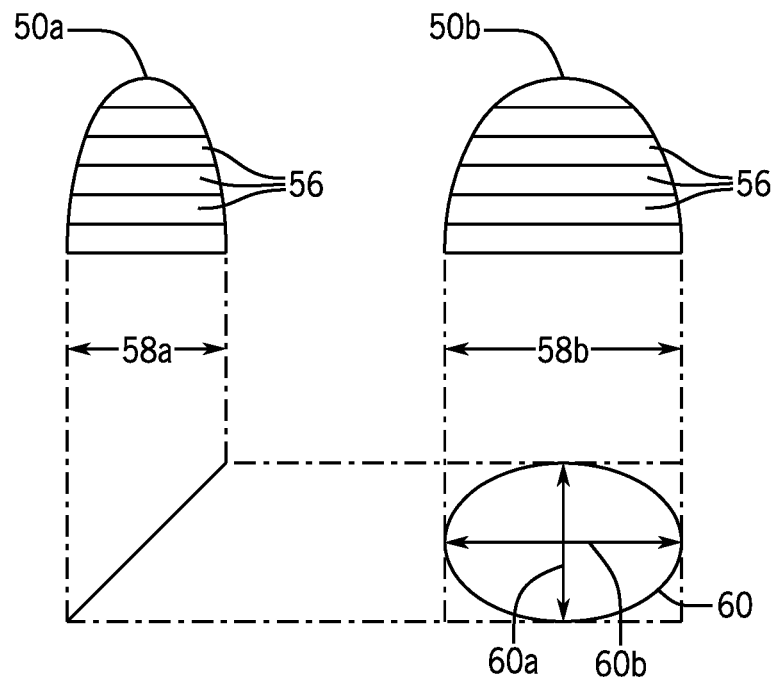
FIG. 3 is a diagrammatic representation of two side views taken by the camera and mirror cone of FIG. 1 as divided into slice regions and showing the use of the slice dimensions to constrain major and minor axes of a fit ellipse.
Figure 4:
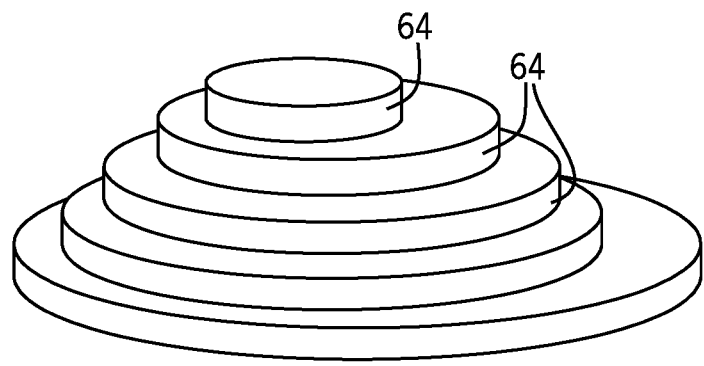
FIG. 4 perspective representation of a volume approximated by stacked ellipsoidal slices.

Referring now to FIG. 3 the profiles 50a and 50b may be processed by the microcontroller board 40 to divide the profiles 50 into a set of two-dimensional slices 56 each generally parallel to the skin plane 22 and including a fixed, predetermined vertical thickness, for example, from 2 to 3 mm. A volume of the lesion 18 may be deduced by looking sequentially at each slice and using a slice width 58a of the first profile 50a (measured parallel to the skin plane 22) to define a first axis 60a of an ellipse 62 (here the minor axis) and to use the slice width 58b of the second profile 50b to define a second axis 60b of the ellipse 62 (here the major axis). The area of that ellipse is calculated by a standard formula and the volume computed by multiplying this area by the slice vertical thickness to calculate a volume of an ellipsoidal slice 64 (shown in FIG. 4). This process is repeated for each slice 56 and the volumes of the ellipsoidal slices 64 summed to create an approximation of the volume of the lesion.

It will be appreciated that increased accuracy can be obtained by decreasing the slice width to the limits of resolution of the camera 30.

Figure 5:
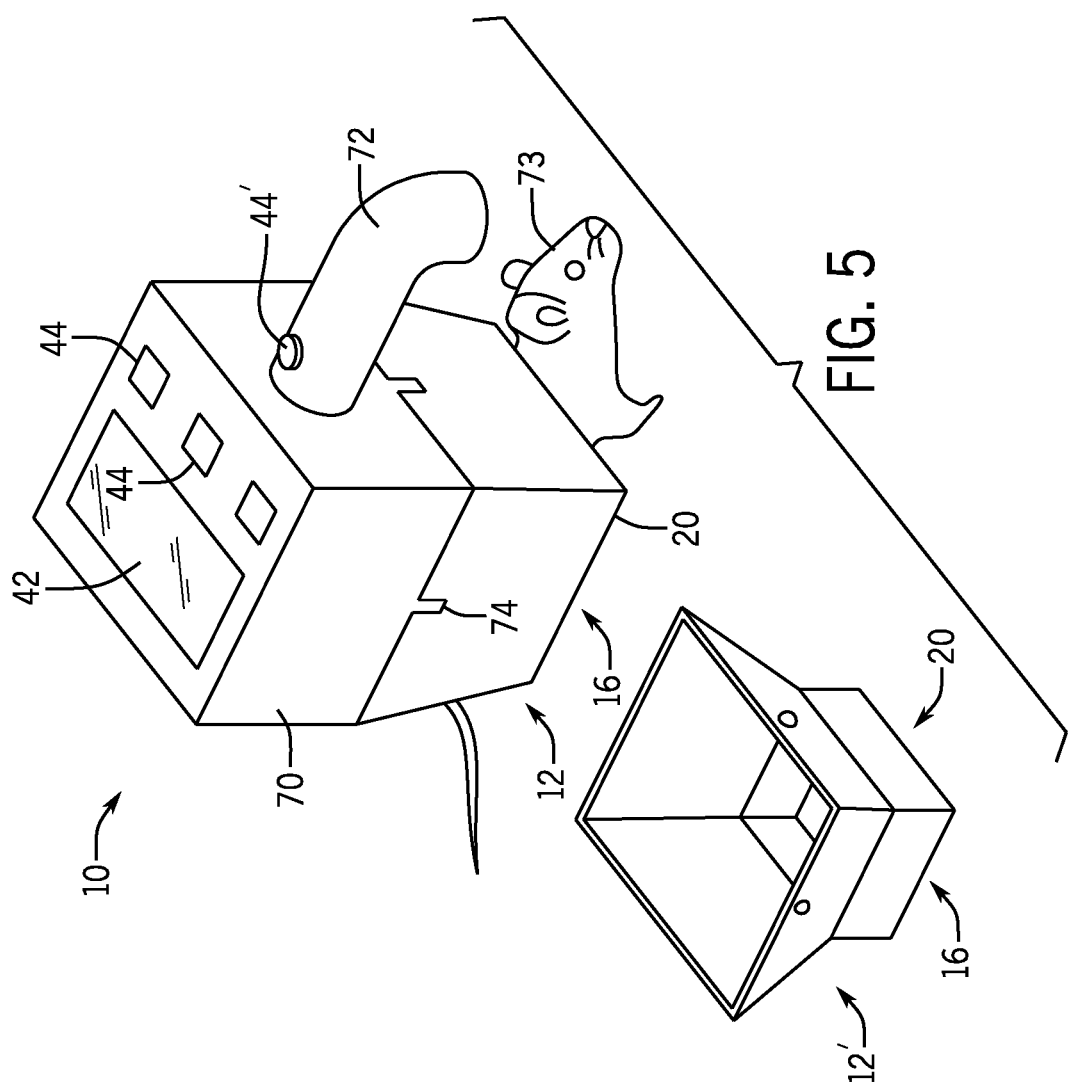
FIG. 5 is a perspective view of an instrument housing for use on laboratory animals showing a replaceable mirror cone for different sized lesions and/or different sized animals.

Referring now to FIG. 5, instrument 10 may further include a main housing 70 containing the battery 47 and microcontroller board 40, diffuse light source 32, and camera 30 (all shown in FIG. 1) and exposing on its upper surface the screen 42 and the switches 44. The main housing 70 may further provide a handle 72 that can be grasped by the hand of a user and that includes a pushbutton switch 44' on a handle 72 operable by the grasping hand. The handle 72 provides for easy single-handed support of the main housing 70 while permitting the user to activate the camera 30 using the pushbutton switch 44' while using a second hand, for example, to stabilize a mouse 73 or the like during the imaging process. More specifically, the user may position the mouse 73 in one hand and place the instrument 10 in proper position over the mouse's lesion 18 by grasping the handle 72.

During positioning of the main housing 60, the screen 42 may provide a real-time view of an image obtained by the camera 30, for example, illuminated by the diffuse light source 32 activated with a partial pressing of pushbutton switch 44'. A full pressing of the pushbutton switch 44' then captures an image and begins the computation of the lesion volume. Several images may be taken and averaged for improved accuracy. Each image will be stamped with a timestamp so that it may be compared to earlier and later acquired images as will be discussed below.

The main housing 70 may connect to the housing 14 of the mirror cone 12, for example, using releasable connector tabs 74 so that a second style of mirror cone 12' can be installed having, for example, a smaller central opening 16 and smaller lower foot surface 20 matched to smaller lesions 18. More generally multiple mirror cones 12 may be provided having different sizes for different animal sizes. Together, the main housing 71 attached to a mirror cone 12 and placed against the skin around the lesion 18 provides an opaque shroud blocking outside light from the lesion 18 providing improved diffuse light elimination free of distracting background and reflections. A switch or sensor (not shown) may inform the microcontroller board 40 of the particular mirror cone 12 being used so as to make the necessary adjustments in the optical magnification provided by a given mirror cone 12. This change in optical magnification results from changes in optical path length and can be readily compensated to provide consistent volume measurements between different mirror cones 12. Alternatively, this information identifying a particular mirror cone 12 may be entered by the user through the switches 44.

Figure 6:
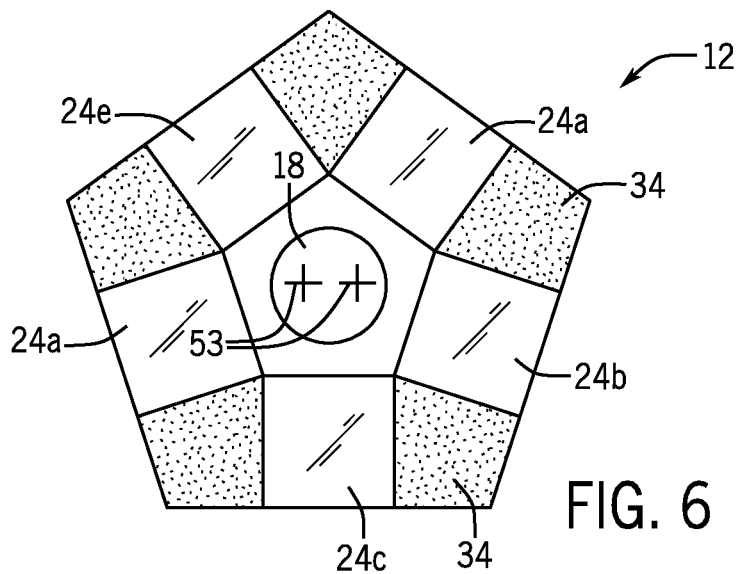
FIG. 6 is a top plan view of an alternative mirror cone design providing for five side views at equal angles about the lesion.
Figure 7:
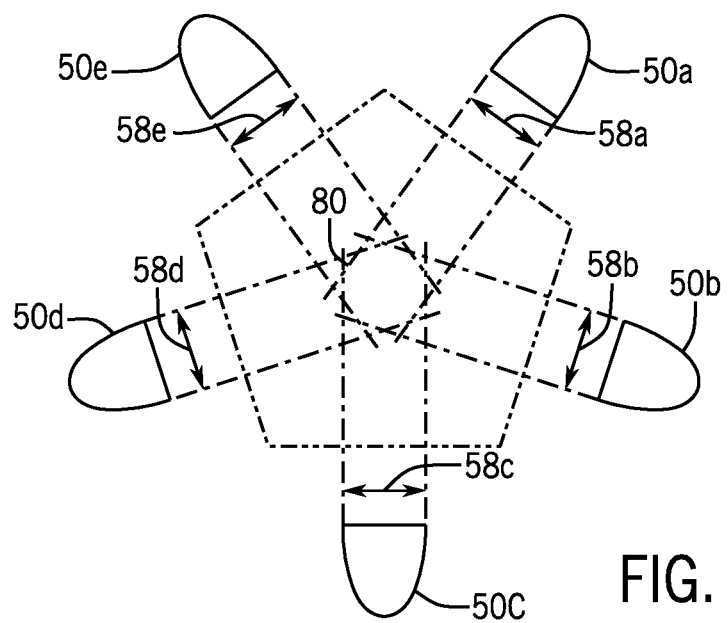
FIG. 7 is a geometric representation of the use of five profiles to describe a convex polygon for calculating a volume of a slice having a convex polygonal periphery or bounding box.

Referring now to FIG. 6, the present invention is not limited to two mirrors 24 but may use an increased number of mirrors 24, for example, mirrors 24a-24e arranged at angular spacings of 72° around the lesion 18 to provide for a larger number of profiles 50a-50e shown in FIG. 7. As before, the regions outside of the mirrors 24 may be coated with a nonreflective material so as to provide a substantially dark background around the lesion 18 for improved imaging. It will be appreciated that in this mirror arrangement each mirror faces primarily a non-mirror surface. In addition, mirrors 24 in the field-of-view of a given mirror 24 can be angled so as to provide images of the mirror box outside of the diffuse light source 32.

Referring to FIG. 7, the profiles 50a-50e may be combined, for example, by projecting widths 58a-58e at the corresponding angles about a center point so that these widths 58a-58e define by their intersection a polygon 80 whose area can be readily computed by geometric means. This area may be used to construct polygonal slices equivalent to the ellipsoidal slices discussed above. Alternatively, a low-order closed curve may be fit to the polygon, the area of that curve computed and used like the ellipsoidal volumes 64 of FIG. 5.

Figure 8:
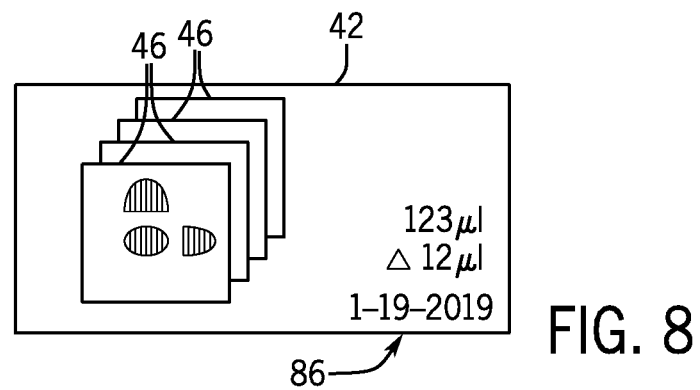
FIG. 8 is a screen representation of a second display mode providing for sequential or video display of multiple images acquired with the present invention for longitudinal analysis.

Referring now to FIG. 8, the screen 42 may operate in different modes, for example, as discussed above to assist in alignment of the instrument 10 with the lesion 18, or as shown in FIG. 8, to display a library of images 46 taken over time, for example, arranged in a stack in chronological order for sequential review, or displayed in rapid succession as a time-lapse video where typically each image 46 is separated by many hours and possibly days. As each image 46 in the stack is displayed volume information and change in volume information as well as timestamp for the time the image was taken can be provided by legends 86.

The images 46 will naturally be registered by an alignment of the alignment marks 52 (shown in FIG. 1) with the tattoo marks 53 on the lesion 18 described above. This registration also avoids variations caused, for example, by lack of centering of the lesion within the central opening 16 or rotation between the lesion 18 and the mirror cone 12 such as may change the dimensions of the profiles.

The volume computed geometrically from the profiles 50 may be corrected by an empirically derived correction factor obtained by making volume measurements per the geometric calculations described above and comparing them to independent volume measurements, for example, made with higher accurate imaging modality. A function relating these two volume approaches may be stored as a curve fit line used for the empirical correction. It is important to note that the volume measurements are used primarily to detect changes and therefore consistency is more important than exact correspondence between the volume of the lesion and the volume computed. For this reason, portions of the lesion below the surface of the skin need not be measured because they will tend to be in proportion to the above skin plane portions.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

The invention claimed is:

1. An apparatus for measuring a volume of a lesion comprising:
   a housing providing a lower surface adapted to be positioned and supported at a surface of skin around the lesion with the lesion extending upwardly through a center opening in the lower surface; the lower surface defining a plane of contact;
   a camera directed toward the center opening along a camera axis, the camera held by the housing at a predetermined distance from the lower surface;
   a first mirror attached to the housing and held at a first angle by the housing;
   a second mirror attached to the housing and held at a second angle by the housing; and
   a computer executing a program stored in non-transitory memory to receive an image from the camera of side views from the first mirror and second mirror to compute the volume of the lesion;
   wherein the first angle and the second angle are such as to direct light received from the lesion and parallel to the plane of contact, to the camera for imaging by the camera;
   wherein the image by the camera through the first mirror and the second mirror excludes portions of the lesion below the surface of the skin; and
   wherein the computer is configured to compute the volume of the lesion limited to a volume above the skin.

2. The apparatus of claim 1, wherein the lower edge of the first mirror furthest from the camera and the lower edge of the second mirror furthest from the camera provide a reflecting surface within one-quarter inch of the plane of contact.

3. The apparatus of claim 1, wherein the image is part of a set of images, wherein the computer is configured to compute the volume of the lesion from an average of the set of images using a sum of a set of slices parallel to the plane of contact at different heights along the lesion and displaced along the camera axis, each slice of the set of slices constrained in width across a first mirror axis and a second mirror axis by a width of the side view from a respective mirror at the height.

4. The apparatus of claim 3, wherein a constraining width of the set of slices is fit to a closed curve to define a slice perimeter; wherein the closed curve is an ellipse, the first mirror axis and the second mirror axis are perpendicular and define a major axis and minor axis of the ellipse, respectively.

5. The apparatus of claim 1, further including a display displaying the image from the camera, the image having at least one fiducial mark superimposed on the image of a top view of the lesion extending upwardly through the center opening and adapted to allow alignment of the lesion with the at least one fiducial mark between successive measurements of the lesion by the apparatus.

6. The apparatus of claim 5, further including at least two fiducial marks to allow both a centering of the lesion within the plane and a predetermined rotational orientation of the lesion about the camera axis.

7. The apparatus of claim 1, wherein the housing provides an opaque shroud around the central opening and further including a diffuse illuminator positioned to illuminate the lesion extending upwardly through the center opening; wherein the diffuse illuminator is a ring light.

8. The apparatus of claim 1, further including a third mirror attached to the housing and held at a third angle by the housing; when the third angle of the third mirror is such as to direct light received parallel to the plane of contact to the camera; and wherein the computer receives the image from the camera of side views from the first mirror, second mirror, and third mirror to compute the volume of the lesion.

9. The apparatus of claim 1, further including a display communicating with the computer to display the image of the lesion together with the computed volume.

10. The apparatus of claim 1, wherein the computer operates to store a set of successive images taken at different times separated by hours together with volumes of the lesions derived from the set of successive images.

11. The apparatus of claim 10, wherein the computer provides a video display sequencing through the set of successive set of images.

12. The apparatus of claim 1, wherein the computer operates to timestamp the image.

13. A method of assessing a volume of a lesion using an instrument having: a housing providing a lower surface adapted to be positioned and supported at a surface of the skin around a lesion with the lesion extending upwardly through a center opening in the lower surface, the lower surface defining a plane of contact; a camera directed toward the center opening along a camera axis, the camera held by the housing at a predetermined distance from the lower surface; a first mirror attached to the housing and held at a first angle by the housing; a second mirror attached to the housing and held at a second angle by the housing wherein the first angle of the first mirror and the second angle of the second mirror is such as to direct light received from the lesion and parallel to the plane of contact, to the camera for imaging by the camera; wherein an image by the camera through the first mirror and the second mirror excludes portions of the lesion below the surface of the skin; and computer executing a program stored in non-transitory memory to receive the image from the camera of side views from the first mirror and the second mirrors to compute the volume of the lesion, the method comprising: (a) positioning the lesion to extend upwardly through the center opening in the lower surface; (b) capturing the side views of only portions of the lesion above the surface of the skin from the first mirror and the second mirror by the computer; and (c) computing the volume of the lesion, limited to a volume above the skin, from the side views and a geometry of the first mirror and the second mirror.

14. The method of claim 13, including repeating steps (a)-(c) at different times separated by hours to obtain a set of time stamped images.

15. The method of claim 13, including playing the set of images as a video sequence.

16. The method of claim 13, including marking the lesion with a lesion mark and aligning the lesion mark with a fiducial mark presented in a camera display of the image.

17. The method of claim 16, wherein aligning includes at least one of translational and rotational alignment between the fiducial mark and the lesion mark.

18. The method of claim 13, wherein the image is part of a set of images, and the method further including the step of averaging together the set of images to obtain the volume of the lesion.

19. The method of claim 13, wherein a number of mirrors is limited to two or three.

20. The method of claim 13, wherein the computer operates to timestamp the image.

* * * * *